(12) United States Patent
Grossi et al.

(10) Patent No.: US 6,197,025 B1
(45) Date of Patent: *Mar. 6, 2001

(54) GROOVED SLIDER ELECTRODE FOR A RESECTOSCOPE

(75) Inventors: Benedetto Grossi; Robert Quint, both of Stamford, CT (US); Richard P. Muller, Bronx, NY (US)

(73) Assignee: Circon Corporation, Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/762,168

(22) Filed: Dec. 9, 1996

Related U.S. Application Data

(63) Continuation-in-part of application No. 08/312,957, filed on Sep. 30, 1994, now Pat. No. 5,582,610.

(51) Int. Cl.⁷ .................................................. A61B 18/18
(52) U.S. Cl. .................................. 606/46; 606/41; 606/49
(58) Field of Search .................................. 607/116, 119, 607/100–102; 600/373; 606/41, 45–50, 11

(56) References Cited

U.S. PATENT DOCUMENTS

| | | | |
|---|---|---|---|
| 642,849 | 2/1900 | Otto . | |
| 3,901,242 | * 8/1975 | Storz | 606/46 |
| 3,990,456 | * 11/1976 | Iglesias | 606/46 |
| 4,095,601 | 6/1978 | Aufranc | 128/405 |
| 4,184,492 | * 1/1980 | Meinke et al. | 606/46 |
| 4,314,559 | 2/1982 | Allen | 128/303 |
| 4,532,924 | 8/1985 | Auth et al. | 128/303.17 |
| 4,726,370 | 2/1988 | Karasaw et al. | 606/46 |
| 4,765,331 | 8/1988 | Petruzzi et al. | 128/303.14 |
| 4,917,082 | 4/1990 | Grossi et al. | 606/46 |
| 5,112,330 | 5/1992 | Nishigaki et al. | 606/46 |
| 5,196,011 | 3/1993 | Korth et al. | 606/46 |
| 5,395,363 | 3/1995 | Billing et al. | 606/41 |
| 5,582,610 | * 12/1996 | Grossi et al. | 606/41 |
| 5,749,870 | * 5/1998 | Gloth et al. | 606/45 |
| 5,766,168 | * 6/1998 | Mantell | 606/46 |
| 5,782,829 | * 7/1998 | Swiantek et al. | 606/46 |
| 5,827,274 | * 10/1998 | Bonnet et al. | 606/41 |

OTHER PUBLICATIONS

The Use Of The Resectoscope In Gynecology, Richard A. Auhll, pp. 91–99, *Biomedical Business International*, Oct. 11, 1990.

Transurethral Vaporization Of The Prostate (T.V.P.); *New Horizons*, Irving M. Bush, M.D., Edward Malthers, M.D. and Janet Bush, R.N.; poster representation; SMIT, Nov., 1993, Orlando, Florida.

* cited by examiner

*Primary Examiner*—Linda C. M. Dvorak
*Assistant Examiner*—David M. Ruddy
(74) *Attorney, Agent, or Firm*—Bradley M. Ganz, Esq.

(57) ABSTRACT

A grooved slider forming part of an electrode for use with a resectoscope is shown. The electrode includes an electrode lead member having an elongated conductor member. The elongated conductor member has a first end and a second end with an insulative cover extended therebetween. The first end has a protruding electrode adapted to be electrically connected to an electrosurgical generator and the second end terminates in an active member. An electrode support member is operatively connected to the active member. The electrode support member has an elongated semi-rigid bifurcated arm terminating in a conductive core spaced a predetermined distance from the active member. The bifurcated arm is covered with an insulative material except at the distal end where the grooved slider is located. The electrode support member has a grooved slider having at least one sloping leading edge surface and protrusions forming areas of increased current densities fixedly mounting the grooved slider on an electrode support member. A method for treating and vaporizing tissue, such as prostate tissue, using the grooved slider electrode for a resectoscope is also shown.

23 Claims, 6 Drawing Sheets

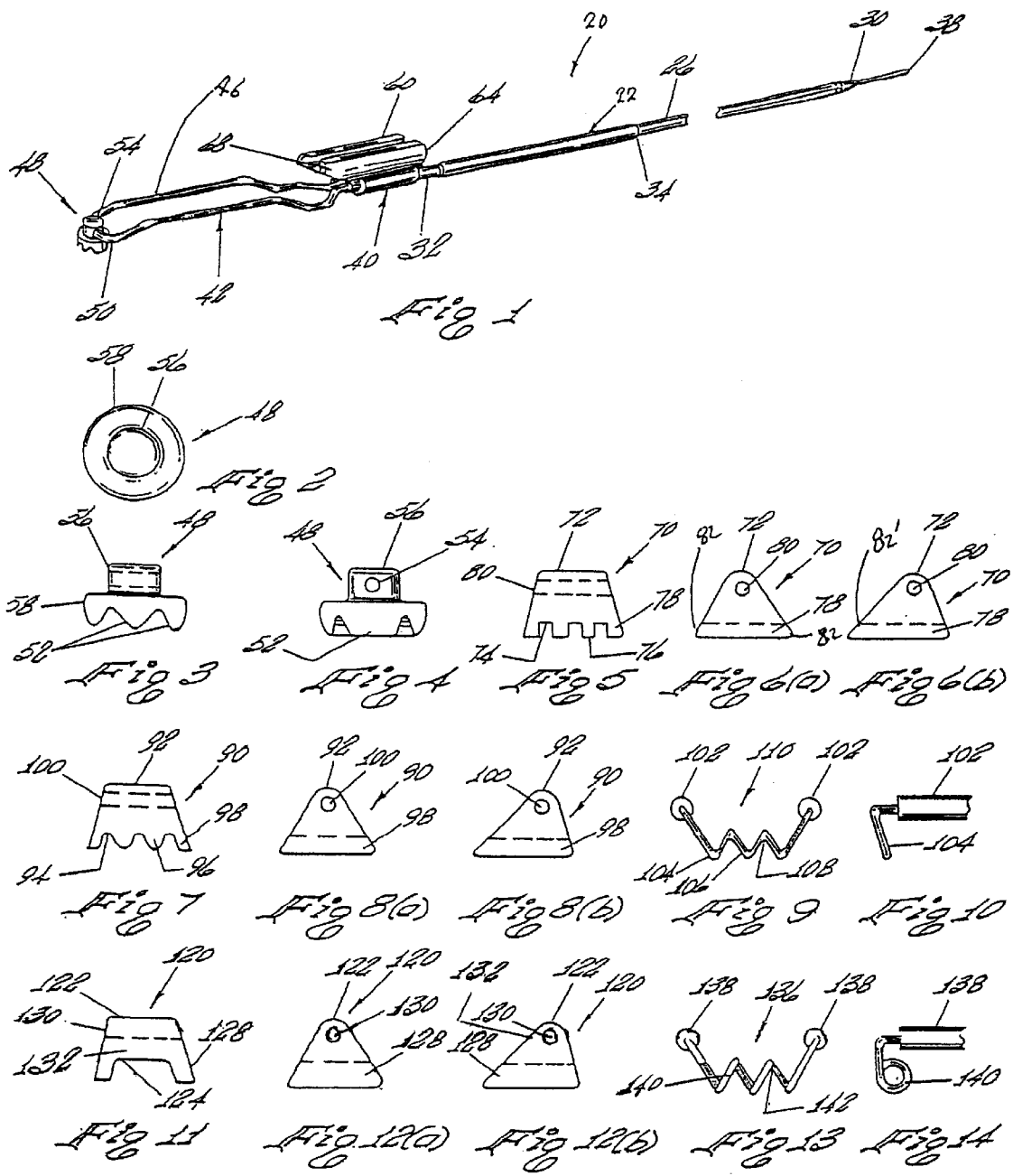

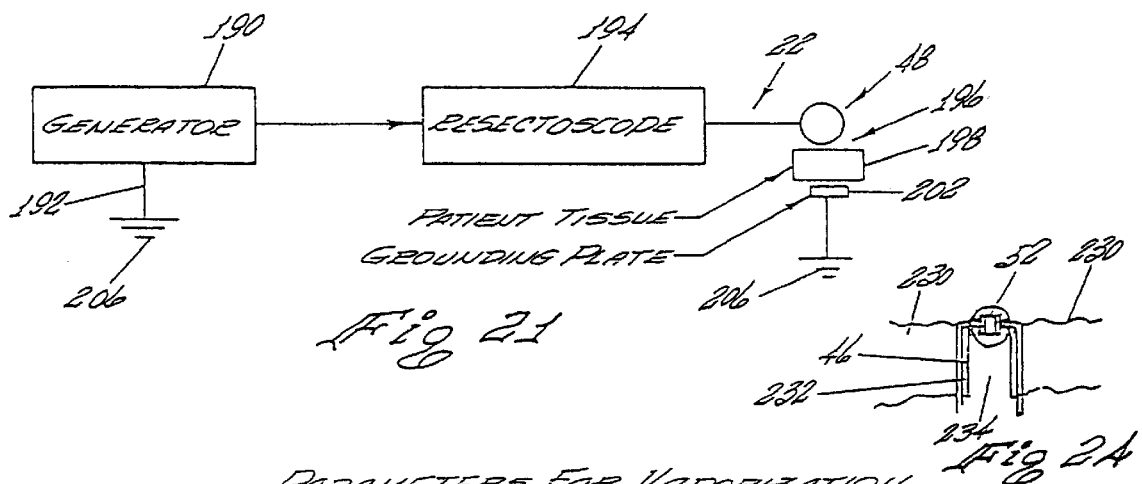
Fig. 21
Fig. 2A
Parameters for Vaporization
| Voltage | Medium | Effect |
|---|---|---|
| 200 V | Air | Cut |
| 300 V | Liquid | Cut |
| 300 V | Air | Charring |
| 400 V to about 500 V | Liquid | Charring |
Fig. 22
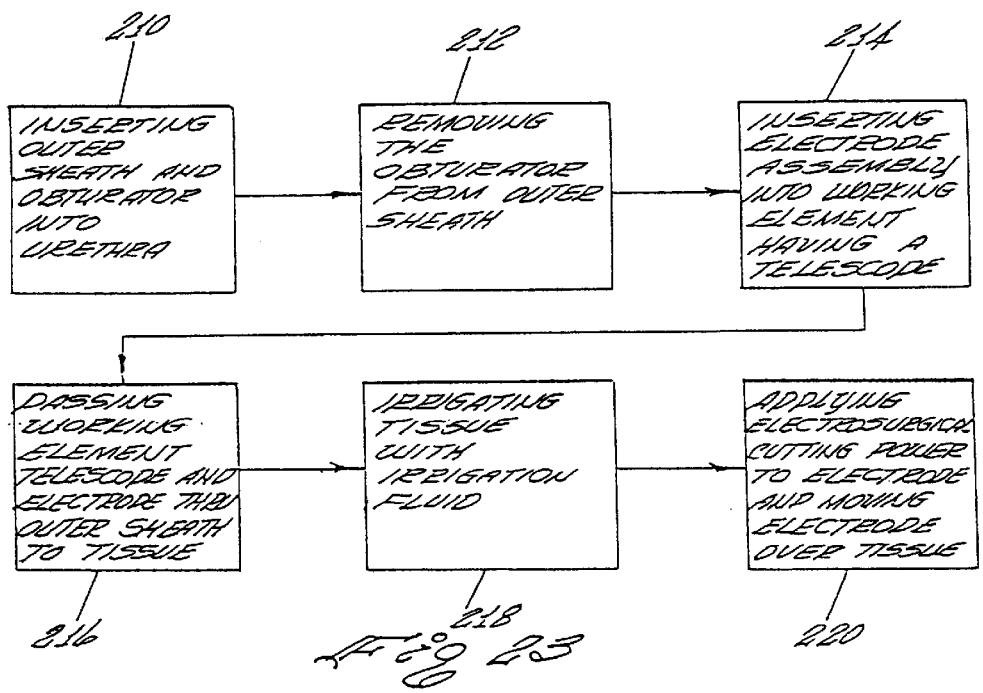
Fig. 23

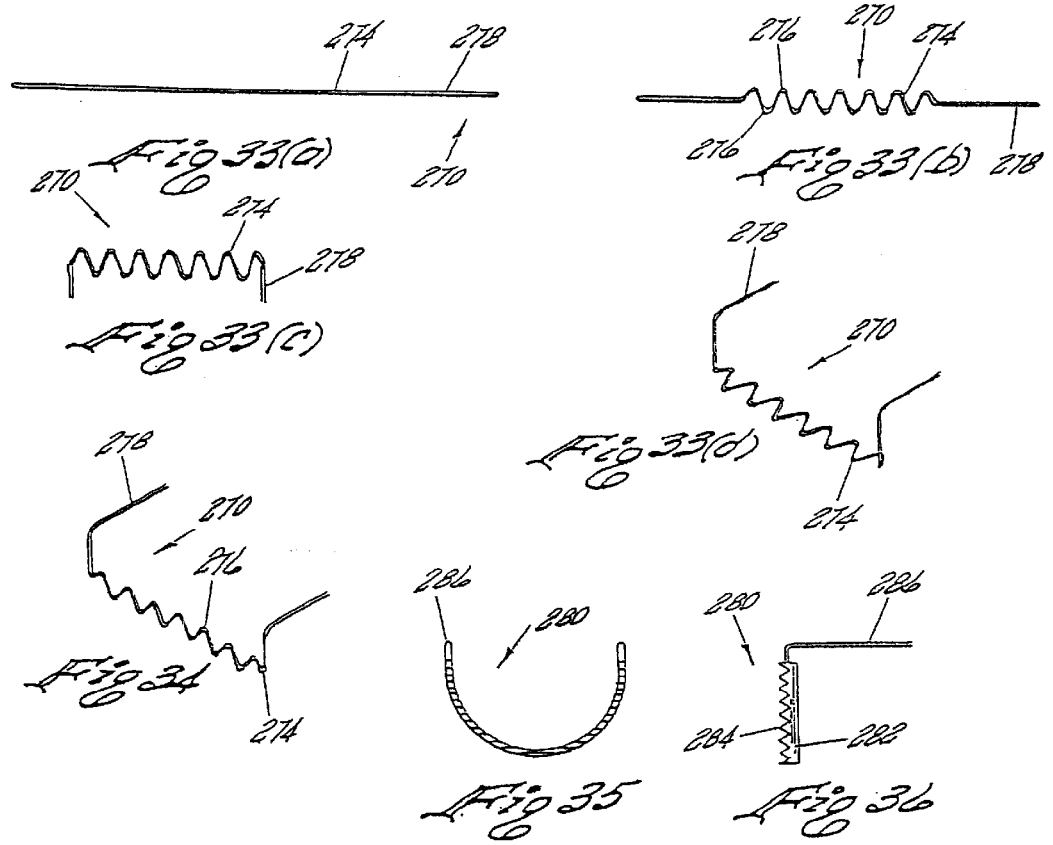

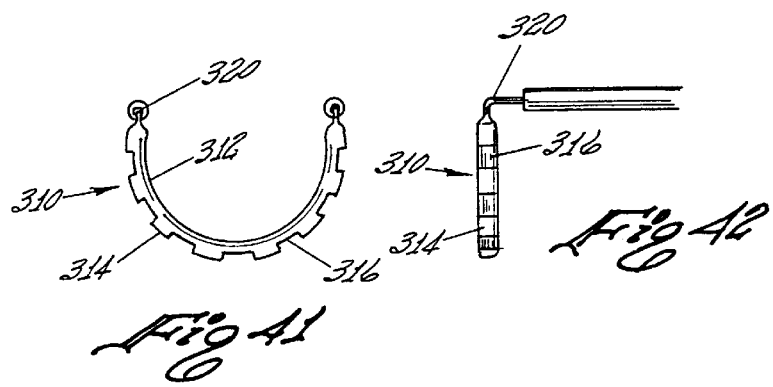
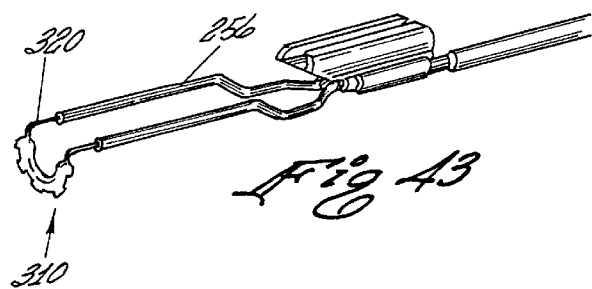
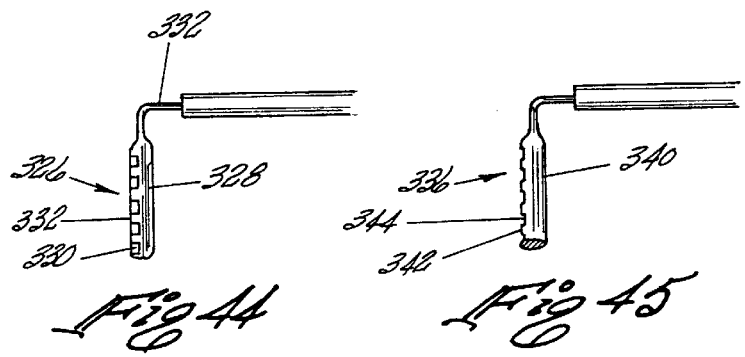
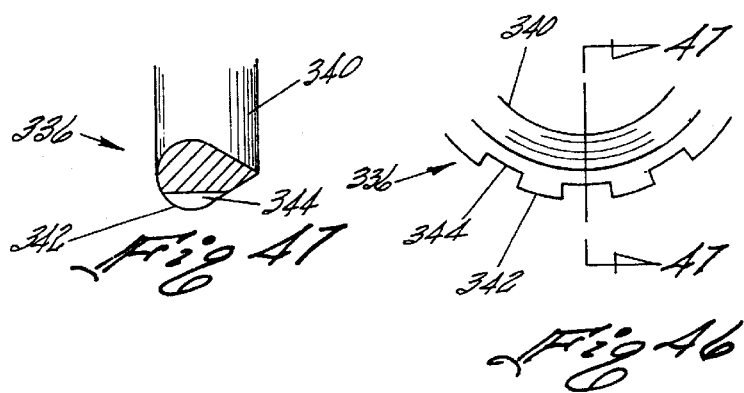

GROOVED SLIDER ELECTRODE FOR A RESECTOSCOPE

RELATED APPLICATION

This application is a Continuation-in-Part of Ser. No. 08/312,957 filed Sep. 30, 1994 which is now U.S. Pat. No. 5,582,610.

BACKGROUND OF THE INVENTION

1. Field of the Invention

The invention relates generally to an electrode having a slider element adapted for use with an endoscope for tissue ablation and more particularly relates to an electrode having a grooved slider for use in performing procedures, such as, for example, in the genitourinary tract on soft tissue, including bladder and prostrate, for hemostasis, incision, excision and ablation or in performing gynecological procedures such as endometrial ablation.

2. Description of the Prior Art

Use of resectoscopes to treat tissue in the genitourinary tract is well known. Typical of such resectoscopes are the devices disclosed in U.S. Pat. Nos. 5,151,101 and 4,955,884.

Resectoscopes used for transurethral resection of the prostate (TURP) have four elements, a resectoscope sheath, sometimes referred to as a sheath or an outer sheath, a working element, an electrode and a telescope. The electrodes are operatively connected to a working element and a telescope is slideably inserted through the working element and into position along side of the electrode. Certain electrodes include an electrode stabilizer which is adapted to receive the telescope. The so assembled working element, telescope and electrode are removable inserted into the sheath to perform a procedure.

In a typical urological procedure, the outer sheath, having an obturator and telescope inserted therein, is visually passed through the urethra to the vicinity of the prostrate and/or bladder neck. The electrode, which is also known as a resectoscope electrode, is typically in the form of a cutting loop located at the distal end of an electrode lead member.

An electrosurgical current, which may be either a coagulation current, a cutting current or some blend thereof is applied to the cutting loop. The energized cutting loop is moved across and cuts the tissue being treated. The cutting loop can also be used to coagulate the wound. In urological procedures, the peak voltage of the electrosurgical cutting currents are typically in the range of 225 volts to about 250 volts at a power level of between about 120 watts to about 200 watts.

A resectoscope electrode having a stabilized cutting loop for a resectoscope is described in U.S. Pat. No. 4,917,082.

The resectoscope electrode described in U.S. Pat. No. 4,917,082 is adapted for use with a urological endoscope or resectoscope. The electrode comprises an electrode lead, an electrode end and an electrode stabilizer. U.S. Pat. No. 4,917,082 discloses that the electrode may take the form of a coagulating electrode, knife electrode, retrograde knife electrode, punctate electrode or roller electrode having a smooth exterior surface.

Continuous flow resectoscopes which utilize a cutting loop electrode for urological procedures are well known in the art and an example of a continuous flow resectoscope is disclosed in U.S. Pat. No. 3,835,842.

An article entitled "THE USE OF THE RESECTO-SCOPE IN GYNECOLOGY" by Richard A. Auhll which appeared at pages 91 through 99 of the Oct. 11, 1990 issue of Biomedical Business International (the "Auhll Reference") disclosed the use of a uterine resectoscope system in the form of a continuous flow resectoscope using an electrosurgical electrode for performing intrauterine procedures.

The Auhll Reference discussed three electrode structures, namely: (1) an electrosurgical cutting loop to treat fibroid tissues; (2) a roller ball having a smooth exterior surface for endometrial ablation (which is cauterization of the endometrium); and (3) electrosurgical needle to cut through and destroy tissue producing intrauterine synechia. In gynecological procedures, the voltage of the electrosurgical cutting currents are typically in the range of 225 volts to about 250 volts at a power level of between 60 watts and 100 watts.

In order to increase the efficiency of treatment of the prostrate tissue generally, and the treatment of benign hypertrophy of the prostrate (BPH) in particular, several new procedures and devices have been developed. These procedures and devices include the use of a Nd:YAG laser for the coagulation and vaporization of prostate tissue generally referred to as abdominal tissue. In order to use Nd:YAG lasers for treatment of BPH, optical fibers capable of deflecting a Nd:YAG laser energy beam about 70° to about 90° to the axis of the optical fiber (generally known as side-firing fibers) have been developed.

Use of a direct contact laser fiber is discussed in an article entitled "TRANSURETHRAL EVAPORATION OF PROSTATE (TUEP) WITH ND:YAG LASER USING A CONTACT FREE BEAM TECHNIQUE: RESULTS IN 61 PATIENTS WITH BENIGN PROSTATIC HYPERPLASIA" by Perinchery Narayan, M.D., George Fournier, M.D., R. Indudhara, M.D., R. Leidich, M.D., K. Shinohara, M.D. and Alex Ingermann, M.D. which appeared at pages 813 through 820, in the June, 1994, Volume 43, Number 6, Issue of Urology (the "Narayan et al. Reference"). The Narayan et al. Reference discusses the use of laser surgery for BPH as a promising alternative to traditional TURP. The Narayan et al Reference discloses that in prostate surgery tissue evaporation referred to as Transurethral Evaporation of Prostate Tissue ("TUEP") was achieved by holding the laser fiber in contact with the area to be treated. The TUEP was performed using an Ultraline Laser Fiber manufactured by Heraeus LaserSonics, Milpitas, Calif. The Ultraline Laser Fiber uses a 600 μm internal reflector fiber covered by a quartz glass cap that reflects the Nd:YAG beam at 80 degrees to the fiber axis. This fiber transmits a high-power density beam (spot size of 700 μm and divergence of 17 degrees, giving a power density at 60 watts to 80 watts of 15,600 to 21,231 W/cm$^2$) 1 mm from the fiber tip. A 23 French cystoscope (CIRCON ACMI, Stamford, Conn.) equipped with an 8 French laser bridge and a continuous flow system was used for the procedure.

The results as state in the Narayan et al. Reference was as follows:

"... Tissue evaporation was achieved by holding the laser fiber in contact with the area to be treated, and by dragging at a rate of 1 cm/20 seconds of laser energy delivery. At the beginning of each furrow dragging was commenced one bulling was seen indicating tissue evaporation. Dragging the fiber at a rate of 1 cm/20 seconds resulted in a furrow 5 to 7 mm deep with a 3 to 4 mm rim of coagulated tissue immediately next to it."

Another known prior art device for treatment of prostate tissue was presented at a poster session at the Society of Minimal Invasive Therapy ("SMIT") on Nov. 5, 1993. The poster session was entitled "TRANSURETHRAL VAPORIZATION OF THE PROSTATE (T.V.P.): NEW HORIZONS" by Irving M. Bush, M.D., Edward Malters, M.D. and Jan Bush, R.N. (the "Bush et al. Reference") disclosed the use of an improved scored ball loop produced by CIRCON ACMI Division of Circon Corporation, assignee of the present patent application, with a continuous flow resectoscope for providing transurethral desiccation (vaporization) of the prostrate.

The Bush et al Reference states as follows:

"T.U.D (transurethral desiccation of the prostate) was first described in 1874 by Bottini. Since 1966 we have used this visually controlled exact vaporization of the prostate in over 500 men with benign hypertrophy, cancer and bladder neck disease.

In the present method (T.V.P., transurethral vaporization of the prostate) a grooved ball electrode and pure electrosurgical cutting current is used to sculpt out the prostatic bed. T.V.P. has the advantage that it causes little or not bleeding, fluid absorption or electrolyte imbalance. Since the residual desiccated tissue (adequate for pathologic review) is removed at the end of the procedure, there is no slough or delayed bleeding (open vessels are closed without retraction). The patient can leave the hospital, voiding (76%) within the 23 hour observation time in most instances. A new improved scored ball loop (A.C.M.I.) to be used with a continuous flow resectoscope has become available.

T.V.P. is a short procedure without sphincter damage which preserves antegrade ejaculation and has a low (2–3%) subsequent procedure rate. Our experience with the last 100 consecutive patients will be detailed."

For purposes of background in electrosurgical treatment of tissue, there are three basic electrosurgical modes: (a) cutting (dissecting) where tissue is severed by a cutting electrode having a radio frequency ("R.F.") cutting current applied to the cutting electrode and the wounded tissue has a layer of coagulation of about 0.5 mm to about 1 mm beyond the cutting area; (b) fulguration where a ball electrode is positioned above the tissue to be treated and an R.F. arc coagulating current flashes from the ball electrode to the tissue to be treated coagulating the tissue; and (c) desiccation where a smooth ball electrode is held in direct contact with the tissue to be treated and a coagulating current of a selected magnitude is applied to the ball electrode vaporizing the tissue.

The first use of electrosurgical generator for prostatic resection using only an R.F. cutting current was in 1931, and the electrosurgical generator was a McCarthy Surgical Unit Type 504A sold by the Complex Oscillator Corporation (the "McCarthy Surgical Unit"). The McCarthy Surgical Unit was a highly efficient vacuum tube generator producing sustained oscillation of high frequency.

The McCarthy Surgical Unit was capable of being used for numerous procedures including prostatic resection. The McCarthy Surgical Unit manual states the following with respect to prostatic resection:

"With the wide interest shown in the relief of prostatic encroachment by the intravesical route, we offer this apparatus as the only present day means for actuating some of the electrodes used for this purpose. The splendid action of this current in a liquid medium has eliminated the hazard of failure at the current source.

The method advocated by Dr. Joseph F. McCarthy, for whom this apparatus was designed, permits great flexibility and with proper technique, the entire prostatic urethra can be remodeled.

The Stern Resectoscope under the able guidance of Dr. T. M. Davis has been modified for greater durability and effectiveness. Other surgical methods that have required the use of high frequency currents have been spurred to new activity.

Here again the requirements have been fully and adequately met and an excess of power provided that will encourage continued research. Those engaged in this specialty are freed of the limitations imposed by generators hitherto available.

In the practice of urology the McCarthy Unit provides every modality. Every purpose which requires the use of high frequency current is served; fulguration of cysts, papillomata, tumors, etc., coagulation control of bleeding, resection and treatment.

The current supplied by the type 504-A unit although very efficacious in resection, shows no effect on delicate insulating materials, greatly prolonging the useful life of urological instruments and electrodes. The selective foot switch permits hemorrhage control with the same electrode used for resection, without the necessity of changing the controls on the apparatus."

The McCarthy Surgical Unit manual states that the McCarthy Surgical Unit can be used for coagulation as follows:

"The unit generates by one type of current, and the controls merely provide the means for adjusting its intensity. It has been established that the same current that shows such admirable cutting characteristics is also the most effective for coagulation. By virtue of its penetrating quality the time necessary for coagulating tumor masses or malignancies has been greatly reduced. Sections of coagulated areas show a tapering off into unaffected tissue that practically eliminates the possibility of secondary hemorrhage. Tumor masses show a remarkable shrinkage during application, proportional to their fluid content.

The technique used in coagulation with this type of current is the same as used for tissue destruction and for hemorrhage control. The electrode must be placed in contact with the area to be treated before the current is turned on. After treatment the current must be off before the electrode is removed. No attempt should be made to ply the area with sparks. In following this technique there is no possibility of carbonization, and no tissue can adhere to the electrode."

The McCarthy Surgical Unit utilized for coagulation and dissection a smooth ball shaped electrode having a 3/16 inch (4 mm) diameter.

The McCarthy Surgical Unit utilized a control panel having two dials. The first dial was referred to as the Range Selector (R.S.) having three ranges, a low, medium and high, each representing one third of the current output. The second dial was referred as the Current Intensity Control (C.I.C.) and provided smooth linear adjustment over each range. Thus, the Range Selector was a course adjustment and the Current Intensity Control was a fine adjustment. The only current produced by the McCarthy Surgical Unit was a cutting current. The maximum current was in the order of 2,600 milliamperes.

In the McCarthy Surgical Unit, for all operative work, dissection, coagulation, bladder fulguration, prostatic resection and the like, a plate electrode was placed under the patient and connected to an indifferent, terminal which is usually a ground terminal, to ground the patient.

In using the McCarthy Surgical Unit for prostatic resection, bleeding resulting from the removal and vaporization of tissue using high intensity cutting current was controlled by passing the same electrode over the same treated tissue area using a low intensity cutting current for providing coagulation of the treated tissue.

Typically, the resulting coagulation layer of the heated tissue had a thickness in the order of 0.5 mm to about 1 mm which appeared sufficient to stop bleeding.

SUMMARY OF THE INVENTION

A novel, new and unique electrode for a resectoscope for performing urological, gynecological and laparoscopic procedures is disclosed and taught by the present invention. In the preferred embodiment, the electrode comprises an electrode lead member having an elongated conductor member having a first end and a second end with an insulative cover extended therebetween. The first end of the electrode member has a protruding electrode which is adapted to be electrically connected to an electrosurgical generator. The second end of the electrode member terminates in an active member.

The electrode includes an electrode support member operatively connected to the loading member and includes an elongated semi-rigid bifurcated arm terminating in a conductive core spaced a predetermined distance from the active member. In one embodiment, the electrode support member has a grooved slider having a central opening extending therethrough for fixedly mounting the grooved slider on the conductive core. In another embodiment, the grooved slider has a solid core. The grooved slider has at ease one sloping leading edge surface and protrusions forming areas of increased current densities.

Also, a method for treating tissue is shown. The method comprises the steps of: (i) inserting a sheath having a visual obturator into a urethra; (ii) removing the visual obturator leaving the outer sheath in the urethra; (iii) inserting into a resectoscope working element a telescope and an electrode wherein the electrode has an electrode lead member which includes an elongated conductor member having a first end and a second end with an insulative cover extended therebetween wherein said first end has a protruding electrode adapted to be electrically connected to an electrosurgical generator and wherein said second end terminates in an active member and having an electrode support having an elongated semi-rigid bifurcated arm terminating in a conductive core spaced a predetermined distance from the active member and wherein the electrode support member has a grooved slider having at least on sloping leading edge surface and protrusions forming areas of increased current densities and is adapted for fixedly mounting the grooved slider on the hub; (iv) passing the resectoscope working element having the telescope and electrode mounted thereon into the sheath and visually positioning the grooved slider in the proximity of the tissue to be treated; (v) irrigating through the sheath the tissue to be treated with an irrigation fluid; and (vi) applying an electrosurgical cutting current to said grooved slider at a selected voltage level of between about 200 volts to about 300 volts and moving the grooved slider having an electrosurgical cutting current applied thereto over the tissue to be treated to ablate the tissue.

Each of the known prior art devices and method have certain disadvantages.

In performing TURP procedures, a urological procedure using state-of-the-art cutting loop electrodes, the potential of undesirable side effects on the patient such as retrograde ejaculation, incontinence and the required use of a Foley catheter for a relatively long period of time, say in the order of 4 to 5 days or more, are becoming objectionable.

The use of laser fibers for treatment of prostatic tissue appears to have less traumatic effect on the patient. However, the efficiency of the procedure in terms of quantities of tissue removed, the technique for using the laser fibers, energy required in joules for vaporizing tissue and the resulting depth of the coagulated layer of tissue are deemed to be short comings to the potential long term use of laser fibers for laser prostatectomy.

The use of scored roller electrode in a resectoscope for treatment of prostatic tissue using cutting current R.F. signals appeared to show that a scored roller ball electrode would successfully vaporize prostatic tissue. However, the removal rate of tissue, the time required for completion of a procedure and the depth of the layer of coagulated tissue appeared to require significant improvement to increase the efficiency of the procedure relative to a laser fiber used for a similar procedure.

Therefore, the problem with the known prior art devices is that the operable power levels in terms of watts are higher than desired using a standard roller ball or a scored roller ball, the size of the craters of vaporized tissue formed in a unit of time is below the desired time verses vaporization results of tissue treatment, the time required to produce trenches of vaporized tissue is longer than desired and the thickness of remaining coagulated tissue is thinner than desired and requires additional coagulating time to develop a sufficient thick coagulate layer of tissue in the area of the treated vaporized tissue.

The grooved slider electrode of the present invention overcomes several of the problems associated with prior and electrodes and devices. The preferred embodiment of the present invention is in the form of a grooved slider which is fixedly attached to the conductive core. In the preferred embodiment, the treating surface has a plurality of raised rails which are capable of vaporizing tissue. In another embodiment, the grooved slider has at least one sloping leading edge surface and protrusions forming areas of increased current densities.

One advantage of the present invention is that the electrode having the grooved slider can be used with standard urological and gynecological resectoscopes.

Another advantage of the present invention is that the grooved slider may have a variety of geometrical shapes such as, for example, planar base having a support surface and a treating surface wherein the treating surface includes a connecting member for rigidly attaching the slider electrode to a conductive core. The treating surface may have a plurality of spaced raised rails having at least one sloping leading edge surface and protrusions forming areas of increased current density. The spaced raised rails may be in form of a plurality of spaced parallel rails. Also, the slider electrode can be in form of a sawtooth member. Alternatively, the treating surface could be in the form of a plurality of substantially parallel conically shaped teeth having a selected height and space formed therebetween. Another configuration is to form the treating surface into two sections, each of which have a different member of parallel rails and elongated spaces therebetween. It is desirable for the electrode configuration to have a large number of high current density areas.

Another advantage of the present invention is that the use of ridges, sawtooth teeth or conically shaped teeth having areas which maximize R.F. current concentration facilitate reduced power requirement, lower power settings on the electrosurgical generator and improved efficiency.

Another advantage of the present invention is that the protruding rails or teeth may have polished surfaces which minimize tissue sticking or adhesion. Thus, as the grooved slider is moved over tissue during treatment, the absence of tissue adhering to the surface of the protruding rails or teeth is desirable to maintain efficiency of vaporization.

Another advantage of the present invention is that the structure of the grooved slider is atraumatic in the non-energized mode.

Another advantage of the present invention is that the grooved slider may be used in urological procedures, gynecological or other procedures requiring tissue vaporization.

Another advantage of the present invention is that the grooved slider can be used with a resectoscope in performing prostatectomy for treatment of BPH of the prostate.

BRIEF DESCRIPTION OF THE DRAWINGS

These and other advantages of the invention will be readily apparent when considered in light of the detailed description hereinafter of the preferred embodiment and of the drawings which include the following figures:

FIG. 1 is a top, front and left side perspective view of a grooved slider electrode for use with a resectoscope;

FIG. 2 is a top view of a grooved slider shown in FIG. 1 having a treating surface formed of a plurality of spaced rails;

FIG. 3 is a front elevational view of a grooved slider shown in FIG. 1;

FIG. 4 is a right side elevational view of the grooved slider of FIG. 2;

FIG. 5 is a front elevational view of another embodiment of a grooved slider having raised rails in the form of substantially rectangular cross-section rails having a selected height and elongated slots formed therebetween;

FIG. 6(a) is a right side elevational view of the grooved slider of FIG. 5;

FIG. 6(b) is a right side elevational view of an eccentric grooved slider having a treating surface similar to that of the grooved slider of FIG. 5;

FIG. 7 is a front elevational view of another embodiment of a grooved slider having raised rails in the form of substantially triangular cross-section rails having a selected height and elongated slots formed therebetween;

FIG. 8(a) is a right side elevational view of the grooved slider of FIG. 7 which defines at least one sloping leading edge surface and protrusions forming areas of increased current densities;

FIG. 8(b) is a right side elevational view of an eccentric grooved slider which defines at least one sloping leading edge surface and a treating surface similar to that of the grooved slider of FIG. 8(a);

FIG. 9 is another embodiment of a grooved slider wherein the electrode is in the form of a sawtooth member having a plurality of spaced, triangular shaped slots having a selected depth forming a treating surface having at least two spaced ridges;

FIG. 10 is a right side elevational view of the grooved slider of FIG. 9;

FIG. 11 is a front elevational view of another embodiment of a grooved slider having a treating surface in the form of single, elongated slot defining a trough having raised side rails;

FIG. 12(a) is a right side elevational view of the grooved slider of FIG. 11;

FIG. 12(b) is a right side elevational view of an eccentric grooved slider having a treatment surface similar to that of the grooved slider of FIG. 11 which defines at least one sloping leading edge surface and protrusions forming areas of increased current densities;

FIG. 13 is a front elevational view of another embodiment of a grooved slider wherein the electrode is in the form of a plurality of spaced parallel teeth formed by a spiral shaped electrode;

FIG. 14 is a right side elevational view of the grooved slider of FIG. 13;

FIG. 21 is a block diagram of a method for using the grooved slider electrode in a urological procedure;

FIG. 22 is a chart showing parameters for vaporization;

FIG. 23 is a block diagram showing the steps of a method for practicing this invention;

FIG. 24 is a diagrammatic representation of a trough formed in a patient tissue using an electrode member of this invention;

FIG. 33(a) is a top plan view of a shaped electrode having an electrode member having opposed shaped protrusions defining a leading edge and trailing edge prior to shaping of the shaped electrode to form a pair of spaced opposed conductive support leads;

FIG. 33(b) is a front plan view of the shaped electrode of FIG. 33(a);

FIG. 33(c) is a top plan view of a shaped electrode having a pair of spaced opposed conductive support leads for supporting a shaped electrode with areas of protrusions formed therein;

FIG. 33(d) is a top, right end and front perspective view of the shaped electrode FIG. 33(b) formed with the spaced opposed conductive support leads having shaped electrode member formed with shaped protrusions defining the leading edge and trailing edge which extend substantially parallel to the direction of movement of the shaped electrode;

FIG. 34 is a top, right end and front perspective view of the shaped electrode of FIG. 33(b) formed with the shaped electrode member having opposed shaped protrusions defining the leading edge and trailing edge which extends substantially to perpendicular to the direction of movement of the electrode;

FIG. 35 is a front elevational view of a shaped conductive core electrode member wherein the shaped leading edge is in the form of a plurality of sharp edges for forming a plurality of areas of high current density when an R.F. electrosurgical current is applied thereto and which extend away from the bifurcated to form a trailing edge for the shaped conductive core electrode member;

FIG. 36 is a sectional view taken along section lines 36—36 of FIG. 35;

FIG. 37 is a front, left end and top perspective view of an electrode of having the shaped conductive core electrode member of FIG. 35 having a plurality of sharp teeth extending away from the bifurcated arm;

FIG. 38(a) is a top plan view of the shaped conductive core electrode member of FIG. 36 prior to forming the electrode and rigidly affixing the same to the bifurcated arms as illustrated in FIG. 35 and showing a pair of spaced opposed conducting support leads operatively connected to the shaped conductive core electrode member wherein the width of the shaped conductive core electrode member is greater than the width of the spaced opposed conducting support leads;

FIG. 38(b) is a front plan view of the shaped conductive core electrode member illustrated in FIG. 38(a) showing that the thickness of the spaced opposed conducting support leads is substantially equal to the thickness of the shaped conductive core electrode member;

FIG. 39 is a front, right end and top perspective view of another embodiment of a shaped conductive core electrode member having a plurality of shaped teeth extending towards the bifurcated arm;

FIG. 40(a) is a front plan view of the shaped conductive core electrode member illustrated in FIG. 39 showing that the thickness of the spaced opposed conducting support leads is substantially equal to the thickness of the shaped conductive core electrode member;

FIG. 40(b) is a sectional view taken across section lines 40(h)—40(h) of FIG. 40(a) showing that the width of the opposed conducting support lead is substantially equal to the width of the shaped conductive core electrode member;

FIG. 41 is a left end elevational view of a grooved slider shaped conductive core electrode member having a plurality of parallel groves forming protrusion areas for developing a plurality of areas of high current density when an R.F. electrosurgical support is applied thereto;

FIG. 42 is a front plan view of the electrode of FIG. 41;

FIG. 43 is a top, left end and front perspective view of the electrode of FIG. 41;

FIG. 44 is a left side elevational view of another embodiment of a shaped conductive core electrode member having at least one sloping leading edge surface and protrusion forming areas of high current densities;

FIG. 45 is a partial cross-sectional left side elevational view of another embodiment of a shaped conductive core electrode member having at least one sloping leading edge surface and protrusion forming areas of high current densities;

FIG. 46 is a pictorial representation of a section of the shaped conductive core electrode of FIG. 45; and FIG. 47 is a pictorial representation of a cross-sectional view taken along section lines 47—47 of FIG. 46.

DESCRIPTION OF THE PREFERRED EMBODIMENT

Figure 15:
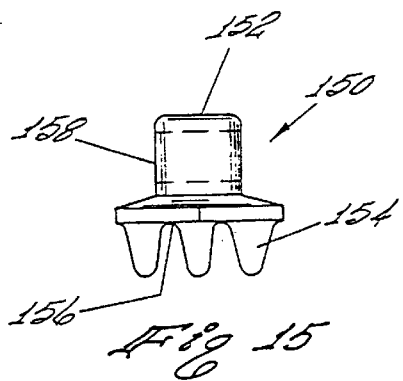
FIGS. 15, 16 and 17 illustrate another embodiment of a grooved slider having a treating surface in the form of a plurality of spaced substantially parallel conically shaped teeth having a selected height and spaces formed therebetween.

In the perspective view of the grooved roller electrode of FIG. 1 shown generally as 20. The structure of the electrode is for use with a resectoscope. The electrode 20 includes an electrode lead member 22 having an elongated conductor member 26 having a first end 30 and a second end 32. An insulative cover 34 extends between the first end 30 and the second end 32.

The first end 30 has a protruding electrode 38 which is adapted to be electrically connected to an electrosurgical generator. The second end 32 in this embodiment terminates in an active member or a loading member shown generally as 40.

In this embodiment, the active member 40 has an electrode support member, shown generally as 42, operatively connected to the loading member 40. The electrode support member 42 has an elongated semi-rigid bifurcated arm 46 which terminates in a conductive core 50 spaced a predetermined distance from the active member 40. The bifurcated arm 46 has an insulative covering formed thereon except in the portion thereof which forms the conductive core 50.

In this embodiment, the electrode support member 42 has a grooved slider 48 having a central opening 54 extending therethrough for fixedly mounting the grooved slider 48 on the conductive core 50.

In the preferred embodiment, the electrode stabilizer 60 for stabilizing the grooved slider is proximate a distal region of a telescope mounted in a resectoscope working element. It is envisioned that the electrode 20 does not need the electrode stabilizer 60 in order to practice this invention. The distal end of a telescope is removably supported by stabilizer 60. The stabilizer 60 has a pair of space resilient support arms 64 which define a hollowed out space 68 to receive a telescope.

The stabilizer 60 may be made of a resilient and flexible dielectric material, generally an insulating material, and resiliently literally mount the electrode to a telescope and insulates the electrode 20 from a telescope. In the alternative, the stabilizer 60 may made of a metal material, such as stainless steel (but could be made of a dielectric material as well as stated above) and maintains alignment of the electrode 20 from a telescope.

FIGS. 2, 3 and 4 depict another embodiment of a grooved slider 48 generally in the form of a planar base 58 having a support surface which includes a connecting member. The connecting member has a central opening 56 for receiving the conductive core 50 and for rigidly attaching the grooved slider to the conductive core 50. The grooved slider has a treating surface having a plurality of spaced raised rails 52. The typical depth of the rails 52 would be in the order of 0.012 inches (3 mm) and the width of the slots therebetween would be in the order of 0.015 inches (4 mm). The diameter of the support base would be in the order of 0.115 inches to about 0.160 inches (3 to 4.5 mm).

FIG. 5 illustrates another embodiment of a grooved slider 70 having a trapezoidal front view with a connecting member 72 at the top thereof and a treating surface located on the bottom thereof having raised rails 76. In this embodiment, the treating surface raised rails 76 are in the form of substantially rectangular cross-sectional rails having a selected height and having elongated slots 74 formed therebetween. Raised side rails 78 are formed along the edges of the treating surface.

The grooved slider 70 has a central opening 80 which is adapted to receive and be fixedly attached to the conductive core 50 as shown in FIG. 1.

The right side elevational view of FIG. 6(*a*) illustrates that the grooved slider 70 of FIG. 5 is symmetrical and has a central opening 80 which is adapted to be fixedly attached to the conductive core 50 as shown in FIG. 1. The grooved slider 70 has at least one sloping leading edge 82.

FIG. 6(*b*) illustrates a right side elevational view of an eccentric of a grooved slider similar to that of FIG. 5 which is shown as 70. The grooved slider has a top 72, a central opening 80 and a treating surface which is similar to that shown on FIG. 5. However, the shaped electrode 70 includes a sloping leading edge surface 82'. The raised rails 78 form protrusions defining areas of increased current densities.

FIG. 7 illustrates another embodiment of a grooved slider 90 raised rails in the form of substantially triangular cross-sectional rails having a selected height and having elongated slots 94 formed therebetween. Raised side rails 98 are formed along the edges of the treating surface.

The grooved slider 90 has top 92 defining a central opening 100 which is adapted to receive and be fixedly attached to the conductive core 50 as shown in FIG. 1.

FIG. 8(*a*) illustrates in a side elevational view the grooved slider 90 of FIG. 7. The grooved slider 90 as illustrated in FIG. 7 is symmetrical and has a top 72 and a central opening 100.

FIG. 8(*b*) illustrates a right side elevational view of an eccentric grooved slider 90 which is similar to that of FIG. 7. The grooved slider 90 has a top 72, a central opening 100 and a treating surface which is similar to that shown in FIG. 7. Also, the shaped electrode 90 includes a sloping leading edge surface 94.

FIGS. 9 and 10 illustrate another embodiment of a grooved slider 110 wherein the electrode is in the form of a sawtooth member having a plurality of spaced, triangular shaped slots having a selected depth and vertex or ridge 106 forming a treating surface having at least two spaced ridges. Side conductors 104 are electrically connected to leads 102 which form part of the bifurcated arm 42 illustrated in FIG. 1 as illustrated in FIGS. 9 and 10, the shaped electrode is spiral shaped and defines the shape as illustrated areas 106 which are protrusions forming areas of increased current densities.

FIG. 11 illustrates another embodiment of a grooved slider, shown generally as 120, having a treating surface in the form of a single elongated slot 124 defining a trough having raised side rails 128. The grooved slider 120 has a top 122 and an elongated opening 130 which extends axially through the grooved slider 120. the grooved slider 120 is adapted to be fixedly mounted on the conductive core 50 illustrated in FIG. 1. The shaped electrode 120 includes a sloping leading edge surface 132.

FIG. 12(*a*) illustrates in a right end elevational view of the grooved slider, shown generally as 120 of FIG. 11, is symmetrical and has a central opening 130 which is adapted to fixedly mount the grooved slider 120 to the conductive core 50 as shown in FIG. 1.

FIG. 12(*b*) illustrates a right side elevational view of an eccentrical of a grooved slider similar to that of FIG. 11. The grooved slider 120 has a top 122, a central opening 130 and a treating surface which is similar to that shown in FIG. 11. In FIG. 12(B) the shaped electrode 120 has a sloped leading edge surface 132.

FIGS. 13 and 14 illustrate another embodiment of a grooved slider 136 wherein the electrode is in the form of a plurality of spaced, parallel teeth 140 formed by coils or a spiral of wire 140. The structure of the teeth and the slots forming a treating surface having at least two spaced ridges is similar to the electrode described in FIGS. 9 and 10.

Figure 16:
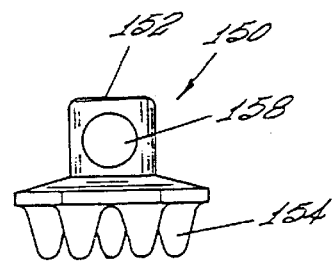
Figure 17:
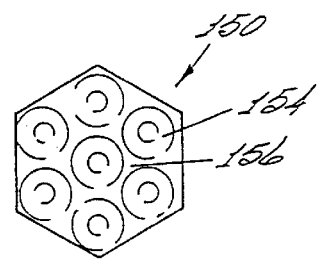

FIGS. 15, 16 and 17 illustrate another embodiment of a grooved slider 150 having a treating surface in the form of a plurality of spaced, substantially parallel conically shaped teeth 154 having a selected height and spaces 156 formed therebetween. The grooved slider 150 has a connecting member having a top 72 and a central opening 158 which is adapted to receive and be fixedly attached to the conductive core 50 as shown in FIG. 1. The shaped teeth 154 are protrusions defining areas of increased current densities.

Figure 18:
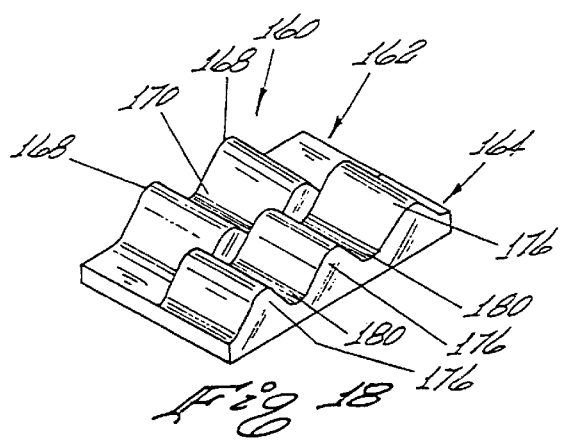
FIGS. 18, 19, 20(a) and 20(b) illustrate another embodiment of a grooved slider having a treating surface in the form of two sections wherein a first section has two parallel rails having selected heights and elongated slots formed therebetween and a second section has three parallel rails having a selected height and elongated slots formed therebetween.
Figure 19:
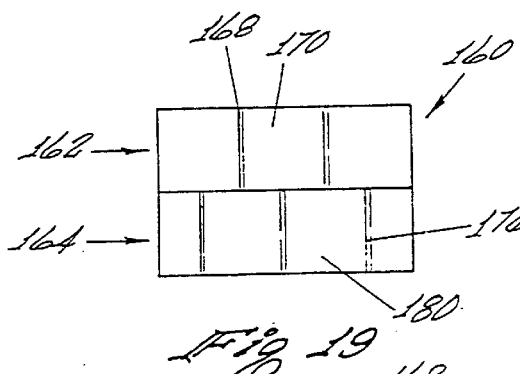
Figure 20B:
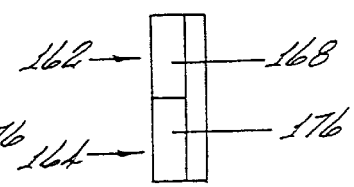
Figure 20A:
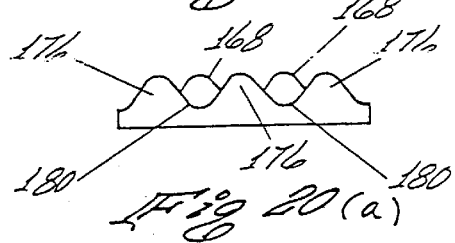

FIGS. 18, 19, 20(*a*) and 20(*b*) illustrate another embodiment of a grooved slider 160 having a treating surface in the form of two sections 162 and 164. The first section 162 has two parallel rails 168 having selected heights and elongated slots 170 formed therebetween, The second section 164 has three parallel rails 176 having selected heights and elongated slots 180 formed therebetween.

The grooved slider 160 is mounted by the surface opposite to the treating surface to the conductive core 30 of FIG. 1.

FIG. 21 is a schematic diagram of an electrosurgical generator 190 which is operatively connected to a resectoscope 194. The electrosurgical generator 190 produces typical R.F. electrosurgical currents which may be a cutting current, a blend current or a loop current. A description of typical R.F. electrosurgical currents is set forth at pages 96 through 97 and page 100 of the ValleyLab SSE4 Instruction Manual.

The electrosurgical current from the electrosurgical generator 190 is applied by the grooved slider electrode 20 and the grooved slider 48 to a patient tissue to be treated, shown by tissue 198.

A dispersive electrode or patient plate, shown as 202, is affixed to the patient, shown by arrow 196, usually by means of a conductive gel. The dispersive electrode 202 is electrically connected to an isolated terminal 206. In order to complete the electrical path back to the electrosurgical generator 190, the electrosurgical generator 190 is electrically connected to the isolated terminal 206.

Thus, the patient 196 is part of the electrically conductive path. As such, the areas of high concentration of R.F. electrosurgical current which form on the protruding ridges, such as, for example, ridges 52 of the grooved slider 48, result in areas of increased current density which electrically interact with the tissue being treated. During treatment, the grooved slider 48 is moved gently over the tissue allowing the grooved slider 48 to move without much pressure, not unlike moving a hot knife through butter, vaporizing the tissue forming a trough therein. This is discussed further in connection with FIG. 23. In this environment, the grooved slider 48 functions as an active electrode while the patient grounding plate functions as a dispersive electrode.

FIG. 22 shows a table of parameters for vaporization using the teachings of the invention. The procedure can be performed with the grooved slider in either air or liquid as a medium. As shown by the table of FIG. 22, air provides less electrical resistance such that an electrosurgical voltage of about 200 volts and a power level of between 160 watts to 240 watts will provide the desired cutting action. An electrical surgical voltage of about 300 volts in air produces charring resulting in a tissue layer having high resistance, which is undesirable.

In liquid and as shown by the table of FIG. 22, an electrosurgical voltage of about 300 volts and a power level of between 160 and 240 watts produces the desired cutting action while an electrosurgical voltage of about 400 volts to about 500 volts produces charring of the tissue.

A method for treating tissue can be performed using the grooved slider of the present invention. FIG. 23 illustrates the steps of the method. The method comprises the steps of inserting a sheath, which may be an outer sheath for a continuous flow resectoscope (CFR), having a visual obturator into a urethra as shown by 210.

The step of removing the visual obturator leaving the outer sheath in the urethra is shown by step 212. Step 214 provides for inserting into a resectoscope working element a telescope and an electrode wherein the electrode has an electrode lead member includes an elongated conductor member having a first end and a second end with an insulative cover extended therebetween wherein said first end has a protruding electrode adapted to be electrically connected to an electrosurgical generator and wherein said second end terminates in an active member and having an electrode support having an elongated semi-rigid bifurcated arm terminating in a conductive core spaced a predetermined distance from the active member and wherein the electrode support member has a grooved slider having a central opening extending therethrough for rotatably mounting the grooved slider on the conductive core. In the alternative, the grooved slider may have at east one sloping leading edge surface and protrusion forming areas of increased current densities.

Step 216 provides for passing the resectoscope working element having the telescope and electrode mounted thereon into the outer sheath and visually positioning the grooved slider in the proximity of the tissue to be treated.

Step 218 provides for irrigating through the outer sheath the tissue to be treated with an irrigation fluid. However, this step is not required if a non-continuous flow resectoscope is used.

Step 220 provides for applying an electrosurgical cutting current to the grooved slider at a selected voltage level of between about 200 volts to about 300 volts.

Step 220 also provides for moving the grooved slider having an electrosurgical cutting current applied thereto over the tissue to be treated to vaporize the tissue.

FIG. 24 is a pictorial representation of a tissue area shown by 230, such as a prostate, wherein the grooved slider 48 supported by bifurcated arm 46 has formed a crater or trough 234 having side walls 232.

In utilizing the grooved slider electrode 48 a shown in FIG. 24, the velocity of movement of the grooved slider 48 in prostate tissue is approximately 5 mm/sec. The depth of the trough (height of side walls 232) is in the order of 3 mm.

Figure 25:
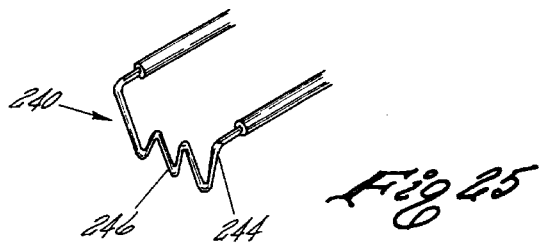
FIG. 25 is a front, right end and top perspective view of a shaped electrode having the plurality of shaped sharp edges similar to the electrode of FIG. 9.

In FIG. 25, the shaped electrode 240 has a conductive electrode member 244 having the plurality of shaped sharp edges 246.

Figures 26, 27, 28:
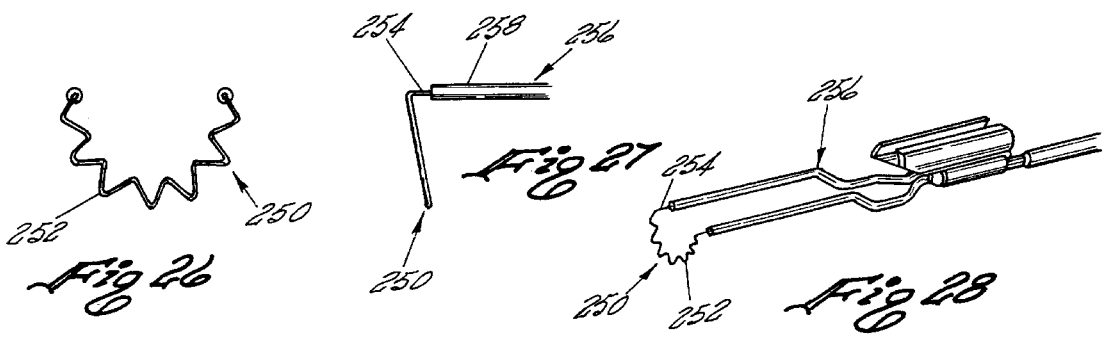
FIG. 26 is a left end elevational view of a star shaped electrode having a plurality of shaped sharp edges and formed into a "U"-shaped electrode member.
FIG. 27 is a right end elevational view of the star shaped electrode 250 of FIG. 26.
FIG. 28 is a front, right end and top perspective view of the electrode of FIG. 27.

In the electrode of FIG. 26, the star shaped electrode 250 is generally "U" shaped and has a plurality of shaped sharp edges 252.

FIG. 27, which is a right end elevational view of the star shaped electrode 250 of FIG. 26, shows a pair of opposed conducting leads 254 operatively connected to a bifurcated arm shown generally as 256. The opposed conducting lead 254 are covered with an insulation covering 258.

Figures 29A, 29B:
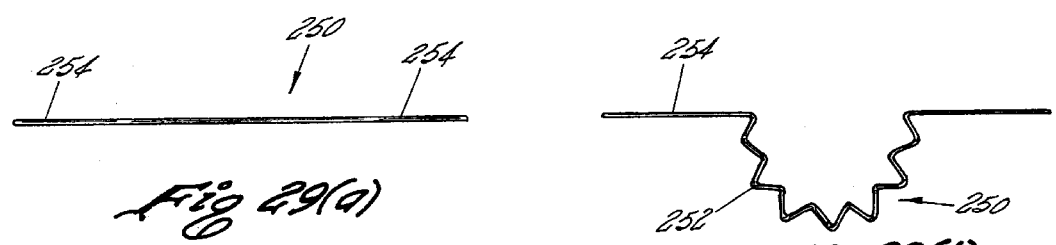
FIG. 29(a) is a top view of the shaped electrode of FIG. 26 prior to forming the electrode and rigidly affixing the same to the bifurcated arms as illustrated in FIG. 28 showing a pair of spaced opposed conducting support leads operatively connected to a star shaped electrode member wherein the width of the star shaped electrode member is substantially equal to the width of the spaced opposed conducting support leads.
FIG. 29(b) is a front plan view of the star shaped electrode member located between the separate leads.

In the front, right end and top perspective view of FIG. 28, the electrode 250 has a "U"-shaped star shaped electrode element having a plurality of shaped sharp edges 252. In FIG. 28, the electrode 250 has the star shaped electrode member 254 operatively connected in a predetermined orientation to the bifurcated arm 256, which, in this embodiment, is substantially normal to the tissue to be treated;

FIG. 29(a) illustrates, in the top view of the star shaped electrode member 250 prior to forming the pair of spaced opposed conducting support leads 254. The support leads 254 are used to operatively connect the star shaped electrode member 250 to the bifurcated arm 256. In FIG. 29(a), the width of the star shaped electrode member 250 is substantially equal to the width of the spaced opposed conducting support leads 254.

In the front plan view of FIG. 29(b), the star shaped electrode member 250 is located between the spaced opposed conducting support leads 254.

Figures 29C, 30, 31:
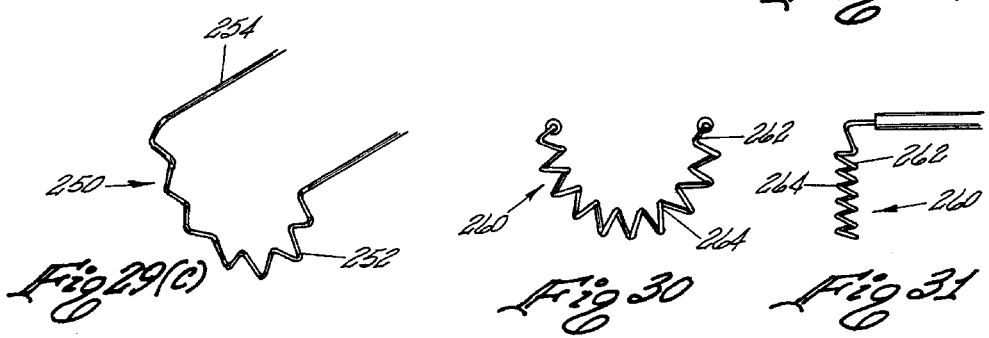
FIG. 29(c) is a front, right end and top perspective view of another embodiment of an electrode member having the plurality of sharp protrusions extending therefrom.
FIG. 30 is a front plan view of another embodiment of a shaped electrode member where the protrusion members are formed by a spiral shaped electrode.
FIG. 31 is a right end elevational view of the spiral shaped electrode of FIG. 30.

In FIG. 29(c), the support leads 254 are formed or deflected so as to position the star shaped electrode member 250 in a predetermined orientation relative to the bifurcated arm 256. In this embodiment, the predetermined orientation is substantially normal to the tissue being treated positioning the star shaped edges 252 in contact with tissue to be treated.

FIG. 30 illustration another embodiment of a shaped electrode member 260 where the protrusion members are formed by a spiral shaped electrode member 262 formed shaped sharp edges 264.

FIG. 31 shows, in a right end elevational view of the spiral shaped electrode member 260 of FIG. 30, that a plurality of sharp edges 264 are formed by the star shaped electrode 260 and are adapted to contact the tissue to be treated.

Figure 32:
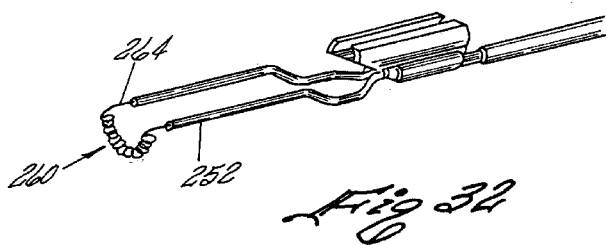
FIG. 32 is a top, right end and front perspective view of the spiral electrode of FIG. 31.

FIG. 32 illustrates the spiral shaped electrode of 260 of FIGS. 30 and 31 operatively attached to a bifurcated arm 252 by conductive support leads 264.

FIGS. 33(a) and 32(b) illustrate a shaped electrode 270 having a generally planar electrode member 274 having opposed shaped sharp protrusions areas 276 define a leading edge and trailing edge. Also, FIG. 33(a) and 33(b) depict the generally planar electrode 270 prior to forming a pair of spaced opposed conductive support leads 278.

In FIG. 33(C), the top plan view illustrates that the pair of spaced opposed conductive support leads 278, which support the electrode having areas of protrusions 276 formed therein, are deflected in the same plane as the areas of protrusions 276.

FIG. 33(d) illustrates that the spaced opposed conductive support leads 278 are deflected or bent to position the shaped electrode member 270 formed with areas of protrusions 272 defining a leading edge and trailing edge which extend substantially parallel to the direction of movement of the shaped electrode 270.

FIG. 34 illustrates that the spaced opposed conductive support leads 278 are deflected or bent to position the shaped electrode member 270 formed with areas of protrusions 272 defining a leading edge and trailing edge which extends substantially to perpendicular to the direction of movement of the electrode 270.

FIGS. 35, 36 and 37 depict a shaped conductive electrode 280 having a shaped conductive core electrode member 282 wherein the shaped leading edge is in the form of a plurality of sharp edges 284 for forming a plurality of areas of high current density when an R.F. electrosurgical current is applied thereto and which extend away from the bifurcated to form a trailing edge for the shaped conductive core electrode member. As shown in FIG. 37, the conductive support arms 286, supporting the electrode member having the plurality of sharp edges 284, are operatively connected to between the bifurcated arm 256 and positioned to have the plurality of sharp teeth 284 extending away from the bifurcated arm 256.

FIGS. 38(a) and 38(b) illustrate another embodiment of a shaped conductive core electrode 290 prior to forming the same into a shaped conductive core electrode member into a "U"-shaped electrode as shown in FIG. 39. In FIGS. 38(a) and 38(b), the shaped conductive core electrode 290 has a pair of conductive support members 296 which supports the shaped conductive core electrode member 292 having a plurality of sharp teeth 294. In the embodiment of FIGS. 38(a), 38(b) and 39, the thickness of the shaped conductive core member 292 is substantially the same as the thickness of the spaced conductive support member 296.

As illustrated in FIG. 39, the shaped conductive core electrode member 290 is formed into a "U"-shaped electrode having a shaped conductive core electrode member 292. The shaped conductive core electrode member 252 is located between the pair of conductive support member 296 and is positioned to have the plurality of sharp teeth 294 extending towards the bifurcated arm 256.

FIGS. 40(a) and 40(b) illustrate another embodiment of a shaped conductive core electrode 300 having a shaped conductive core electrode member 302 located between a pair of spaced conductive support leads 306. The shaped conductive core electrode member 302 has a plurality of sharp teeth 304 extending towards the bifurcated arm 256 (the bifurcated arm 256 being illustrated in FIG. 37). As illustrated in FIG. 40(a) the thickness of the shaped conductive core electrode member 302 is greater than the thickness of the opposed conducting support lead 306.

FIGS. 41, 42 and 43 illustrate another embodiment of a grooved slider shaped conductive core electrode 310 having a grooved slider shaped conductive core electrode member 312. The shaped conductive core electrode member 312 defines a plurality of parallel groves 316 forming protrusion areas 314 for developing a plurality of areas of high current density when an R.F. electrosurgical support is applied thereto.

FIG. 44 illustrates another embodiment of a shaped conductive core electrode member 326 having at least one sloping leading edge surface 328 and protrusions 332 separated by grooves 330 for forming areas of high current densities around the periphery of the trailing edge. A pair of opposed conductive support leads 332 operatively connect the shaped conductive core electrode member 326 between the bifurcated arm 256 (illustrated in FIG. 43).

FIG. 45 illustrates another embodiment of a shaped conductive core electrode 336 having at least one sloping leading edge surface 340 and protrusions 342 formed by grooves 344 for defining areas of high current densities. In this embodiment, the trailing edge of the shaped conductive core electrode 336 has the areas of protrusions located to contact the tissue being treated.

FIG. 46 illustrates, in the pictorial representation of a section of the shaped conductive core electrode 336, that the at least one sloping edge 340 is directed towards the bifurcated arm.

In the cross-sectional view of FIG. 47, the bottom surface of the trailing edge having the grooves 344 and the areas of protrusions 342 is shown in an orientation to directly contact tissue to be treated.

In the preferred embodiment, the method for treating prostate tissue comprises the step of irrigating through an instrument the prostate tissue to be treated and applying a high electrosurgical cutting current to grooved slider at a selected voltage level of between about 200 volts to about 300 volts, and moving the grooved slider having the electrosurgical cutting current applied thereto over a selected portion of prostate tissue to be treated to vaporize the tissue and form a trough having a coagulation layer of treated tissue of at least 2 mm.

FIG. 24 is a pictorial representation of a tissue area shown by 230, such as a prostate, wherein the grooved slider 48 supported by bifurcated arm 46 has formed a crater or trough 196 having side walls 232.

In utilizing the grooved slider electrode 48 a shown in FIG. 24, the velocity of movement of the grooved slider 48 in prostate tissue is approximately 5 mm/sec. The depth of the trough (height of sidewalls 232) is in the order of 3 mm.

The R.F. electrosurgical setting cooperates with the raised ridges or protrusion to form areas of increased current densities which generate sufficient current flow at the appropriate voltage levels to vaporize the tissue. The tissue surrounding the vaporized tissue becomes coagulated by the R.F. electrosurgical current at the boundary of the vaporized tissue resulting in a layer of necrosed tissue around the side walls 232 and trough 234. The thickness of the coagulated layer is in the order of about 1.5 mm to about 2 mm. Energy settings in the range of 160 watts to about 250 watts is desired, with the preferred power settings to be about 200 watts.

The preferred embodiment shown and described herein is directed for use in a urological procedure. This is an exemplary use and it is envisioned that the principle and teaching herein could be adapted for other procedures.

As an example, the electrode structure could be designed for use in a gynecological procedure with a gynecological resectoscope for performing endometrial ablation of the uterus or debulking myomas.

Also, various other configurations for the design of the grooved slider are envisioned and the preferred embodiment and species disclosed and described herein are exemplary and are not intended to restrict the inventor to the exemplary configuration disclosed herein.

What is claimed is:

1. An electrode comprising
a grooved slider having at least one sloping leading edge surface and protrusions having at least two raised edges separated by a groove having a bottom portion and sidewalls extending from said bottom portion of the grooves to the raised edges forming areas of high current densities on a treating surface adapted to contact tissue and wherein said protrusions generate sufficient current flow at known voltage levels to vaporize the tissue, said grooved slider being adapted to be fixedly attached in a predetermined orientation to an electrode support member.

2. The electrode of claim 1 wherein said slider electrode is in the form of a sawtooth member having a plurality of spaced, shaped teeth having a selected depth forming a treating surface having at least one ridge between each adjacent teeth.

3. The electrode of claim 1 wherein the electrode has a treating surface in the form of a plurality of spaced, parallel teeth.

4. The electrode of claim 1 wherein the slider electrode has a treating surface in the form of a plurality of spaced, substantially parallel, conically shaped teeth having a selected height and spaces formed therebetween.

5. An electrode for use with a resectoscope comprising
a grooved slider adapted to be operatively connected to a bifurcated arm and having at least one sloping leading edge surface and protrusions having at least two raised edges separated by a groove having a bottom portion and sidewalls extending from said bottom portion of the grooves to the raised edges forming areas of high current densities on a surface adapted to contact tissue and wherein said protrusions generate sufficient current flow at known voltage levels to vaporize the tissue.

6. The electrode of claim 5 wherein said grooved slider is generally in the form of a planar base having a support surface and a treating surface, said support surface including connecting member having a central opening for receiving said conductive core and for rigidly attaching said grooved slider to a conductive core located between said bifurcated arm and said treating surface having a plurality of spaced raised rails.

7. An electrode for use with a resectoscope comprising
an electrode lead member terminating in an active member;
an electrode support member operatively connected to said active member having an elongated semi-rigid bifurcated arm; and
a grooved slider having at least one sloping leading edge surface and protrusions having at least two raised edges separated by a groove having a bottom portion and sidewalls extending from said bottom portion of the grooves to the raised edges forming areas of high current densities on a treating surface and wherein said protrusions generate sufficient current flow at known voltage levels to vaporize tissue brought into contact with the grooved slider, said grooved slider being fixedly attached in a predetermined orientation to said bifurcated arm.

8. A method for treating tissue comprising the steps of
inserting into a resectoscope working element an electrode having a grooved slider at least one sloping leading edge surface and protrusions having at least two raised edges separated by a groove having a bottom portion and sidewalls extending from said bottom portion of the grooves to the raised edges forming areas of high current densities on a treating surface and wherein said protrusions generate sufficient current flow at known voltage levels to vaporize tissue brought into contact with the grooved slider, said grooved slider being fixedly mounted onto the electrode;
positioning the treating surface of the grooved slider on the tissue to be treated.

9. The method of claim 8 further comprising the steps of
irrigating the tissue to be treated with an irrigation fluid;
applying an electrosurgical cutting current to said grooved slider at a selected voltage level of between about 200 volts to about 300 volts; and
moving the treating surface of the grooved slider having an electrosurgical cutting current applied thereto over the tissue to be treated to ablate the tissue.

10. A method for treating prostate tissue comprising the steps of
positioning a grooved slider having at least one sloping leading edge surface and protrusions having at least two raised edges separated by a groove having a bottom portion and sidewalls extending from said bottom portion of the grooves to the raised edges forming areas of high current densities on the prostrate tissue to be treated and wherein said protrusions generate sufficient current flow at known voltage levels to vaporize tissue brought into contact with the grooved slider.

11. The method of claim 10 further comprising the step of
applying a high electrosurgical cutting current to the grooved slider at a selected voltage level of between about 200 volts to about 400 volts; and
moving the grooved slider having at least one sloping leading edge surface and protrusions forming areas of increased current densities while having the electrosurgical cutting current applied thereto over a selected portion of prostate tissue to be treated to vaporize the tissue and form a coagulation layer in a remaining crater of treated tissue of at least 1 mm.

12. An electrode for use with a resectoscope comprising
an electrode lead member including an elongated conductor member having a first end and a second end with an insulative cover extended therebetween, said first end having a protruding electrode adapted to be electrically connected to an electrosurgical generator, said second end terminating in an active member; and
an electrode support member operatively connected to said active member having an elongated semi-rigid bifurcated arm terminating in a conductive core, said electrode support member having a fixedly mounting in a predetermined orientation on said conductive core a grooved slider having at least one sloping leading edge surface and a treating surface having protrusions having at least two raised edges separated by a groove having a bottom portion and sidewalls extending from said bottom portion of the grooves to the raised edges forming areas of high current densities and wherein said protrusions generate sufficient current flow at known voltage levels to vaporize tissue brought into contact with the grooved slider.

13. The electrode of claim 12 further comprising
an insulative covering applied to the bifurcated arm with the conductive core exposed to fixedly support said grooved slider.

14. The electrode of claim 12 further comprising
an electrode stabilizer for stabilizing the grooved slider proximate a distal region of a telescope, said stabilizer being made of a resilient and flexible dielectric material for resiliently laterally mounting the electrode to a telescope and for insulating the electrode from a telescope.

15. The electrode of claim 12 wherein said grooved slider is generally in the form of a planar base having a support surface and a treating surface, said support surface including connecting member having a central opening for receiving said conductive core and for rigidly attaching said grooved slider to said conductive core and said treating surface has a plurality of spaced raised rails.

16. The electrode of claim 15 wherein the plurality of spaced raised rails are in form of spaced substantially parallel rails.

17. The electrode of claim 15 wherein the rails have a substantially rectangular cross-section and a selected height and wherein elongated slots are formed therebetween.

18. The electrode of claim 15 wherein said rails have a substantially triangular cross-section and a selected height and wherein elongated slots are formed therebetween.

19. The electrode of claim 12 wherein said slider electrode is in the form of a sawtooth member having a plurality of spaced, triangular shaped teeth having a selected depth forming a treating surface having at least one ridge between each adjacent teeth.

20. The electrode of claim 12 wherein the slider electrode has a treating surface in the form of a plurality of spaced, parallel teeth.

21. The electrode of claim 12 wherein the slider electrode has a treating surface in the form of a plurality of spaced, substantially parallel, conically shaped teeth having a selected height and spaces formed therebetween.

22. The electrode of claim 12 wherein said slider electrode has a treated surface in the form of two sections wherein a first section has two parallel rails having a selected height and elongated slots formed therebetween and a second section has three parallel rails having a selected height and elongated slots formed therebetween.

23. The electrode of claim 22 wherein the rails have a substantially triangular shaped cross-section.

* * * * *